(12) United States Patent
Baumgart

(10) Patent No.: US 10,918,370 B2
(45) Date of Patent: Feb. 16, 2021

(54) SUPPORT DEVICE MOUNTABLE TO THE PELVIC BONE

(71) Applicant: Rainer Baumgart, Munich (DE)

(72) Inventor: Rainer Baumgart, Munich (DE)

(73) Assignee: Rainer Baumgart, Munich (DE)

( * ) Notice: Subject to any disclaimer, the term of this patent is extended or adjusted under 35 U.S.C. 154(b) by 20 days.

(21) Appl. No.: 16/457,020

(22) Filed: Jun. 28, 2019

(65) Prior Publication Data

US 2019/0314008 A1 Oct. 17, 2019

Related U.S. Application Data

(62) Division of application No. 15/479,129, filed on Apr. 4, 2017, now Pat. No. 10,485,531.

(30) Foreign Application Priority Data

Apr. 4, 2016 (EP) ..................... 16163669

(51) Int. Cl.
*A61B 17/02* (2006.01)
*A61B 17/56* (2006.01)
(Continued)

(52) U.S. Cl.
CPC ............ *A61B 17/025* (2013.01); *A61B 17/56* (2013.01); *A61F 2/30739* (2013.01);
(Continued)

(58) Field of Classification Search
CPC . A61B 17/025; A61B 2017/0275; A61F 2/32; A61F 2/36
See application file for complete search history.

(56) References Cited

U.S. PATENT DOCUMENTS

| 2,947,308 A | 8/1960 | Gorman |
| 5,702,477 A | 12/1997 | Capello et al. |

(Continued)

FOREIGN PATENT DOCUMENTS

| DE | 295 13 694 U1 | 1/1997 |
| EP | 1371346 A1 | 12/2003 |
| EP | 1 442 727 A2 | 8/2004 |

OTHER PUBLICATIONS

Baumgart et al., "Reduction of high dislocation of the hip using a distraction nail before arthroplasty," J Bone Joint Surg, vol. 87-B, No. 4, Apr. 2005.

(Continued)

*Primary Examiner* — Jason-Dennis N Stewart
(74) *Attorney, Agent, or Firm* — Marshall, Gerstein & Borun LLP

(57) ABSTRACT

A support apparatus for supporting an end of a distraction marrow nail includes a base plate attachable to the pelvis, and a mounting device on the base plate for mounting of the support end of the distraction marrow nail. The mounting device includes a ball seat having a cavity forming a ball seat surface for mounting a ball on the support end of the distraction marrow nail, wherein the inside radius of the ball seat surface corresponds to the outside radius of the ball, and wherein the ball seat is arranged so that the ball of the distraction marrow nail can be movably mounted such that the distraction marrow nail can perform a movement sufficient for an extensively normal movement pattern of a femur and cannot luxate out of the ball seat when implanted in the femur.

10 Claims, 4 Drawing Sheets

(51) Int. Cl.
    *A61F 2/32*     (2006.01)
    *A61F 2/30*     (2006.01)
    *A61F 2/36*     (2006.01)
(52) U.S. Cl.
    CPC ............ *A61F 2/30749* (2013.01); *A61F 2/32* (2013.01); *A61F 2/36* (2013.01); *A61B 2017/0275* (2013.01); *A61B 2017/567* (2013.01); *A61F 2002/3233* (2013.01)

(56) References Cited

U.S. PATENT DOCUMENTS

| | | |
|---|---|---|
| 6,096,083 A | 8/2000 | Keller et al. |
| 6,840,959 B2 | 1/2005 | Treacy et al. |
| 2002/0165615 A1 | 11/2002 | Abouaf et al. |
| 2004/0225370 A1 | 11/2004 | Cruchet et al. |
| 2011/0264216 A1 | 10/2011 | Makower et al. |
| 2012/0253414 A1 | 10/2012 | Gabriel et al. |
| 2014/0257501 A1 | 9/2014 | Lowe et al. |

OTHER PUBLICATIONS

Search Report for European Patent Application No. 16163669.1, dated Sep. 7, 2016.
Office Action for European Patent Application No. 16 163 669.1, dated Oct. 16, 2017.

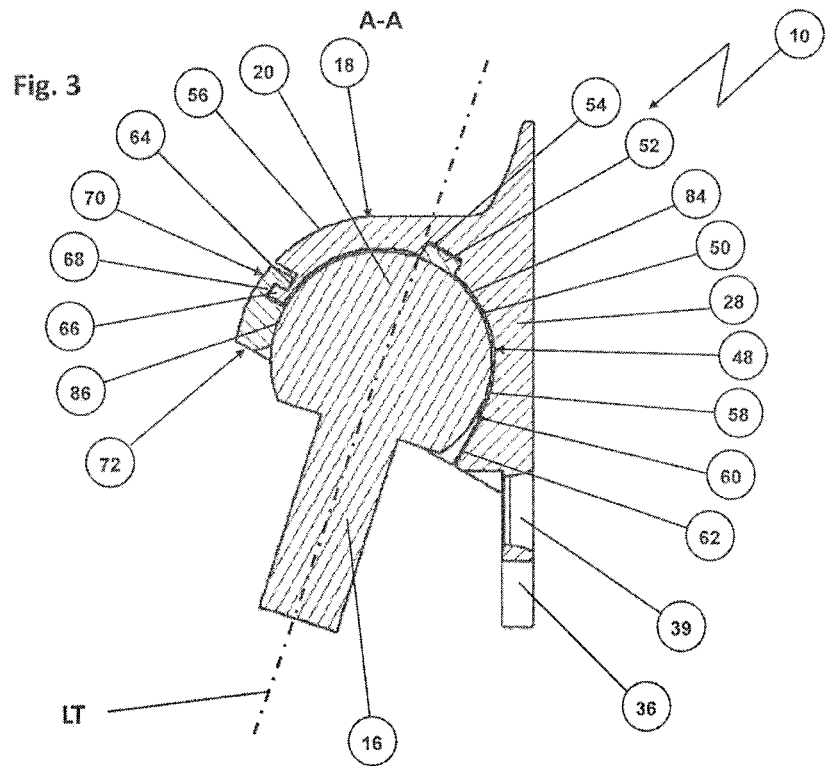
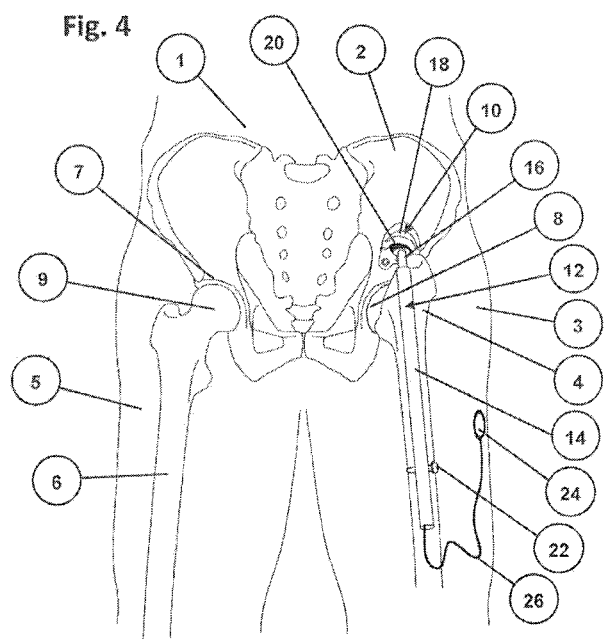
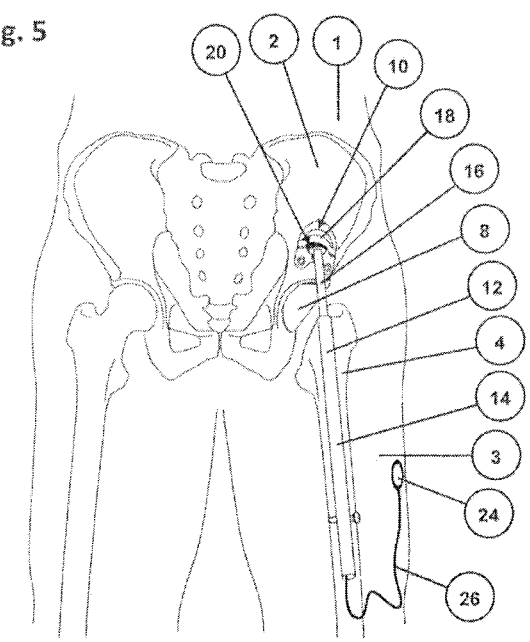

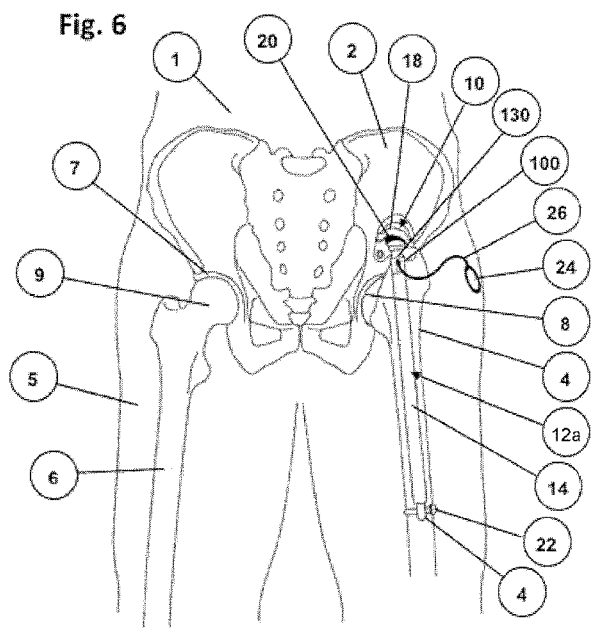
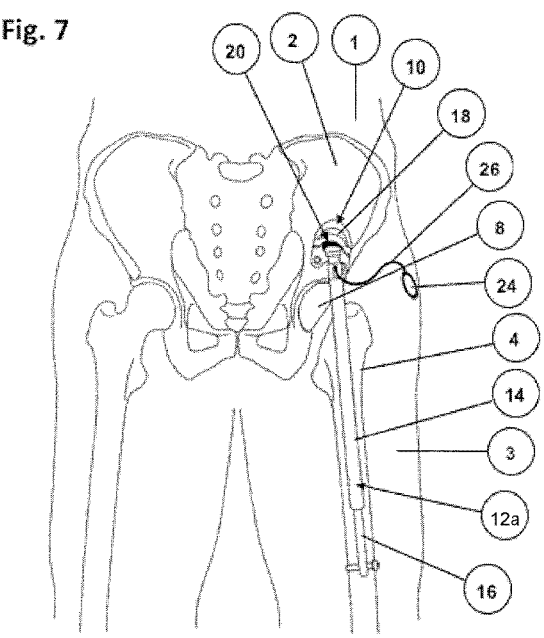

SUPPORT DEVICE MOUNTABLE TO THE PELVIC BONE

FIELD OF THE INVENTION

The invention relates to a support apparatus that can be mounted on the pelvic bone as well as to an apparatus having the support apparatus, for stretching soft tissue parts in the hip region.

SUMMARY OF THE INVENTION

Endoprosthetic hip joint replacement is a widespread operative method if the human hip joint is worn out and severe pain results from this. In this regard, a socket is implanted at the same location where the natural hip joint is placed, in which socket an artificial, round joint head that is anchored in the femur with a shaft can articulate.

If the hip joint has been displaced toward the head (in the cranial direction) due to an incorrectly placed (dysplastic) socket or after an accident event or after a tumor resection, leg shortening regularly takes place, on the one hand, and, on the other hand, a clear restriction of movement generally occurs, with what is called a neo-joint generally forming around the pelvic head, which joint guarantees support that is able to withstand stress.

In the case of such a starting situation, in which the hip joint has migrated toward the head, it has only been possible to implant an artificial hip joint with very unsatisfactory results up to the present, because on the one hand, implantation of an artificial joint in the region of the iliac wing yields very poor long-term results, and, on the other hand, placement of the artificial joint in an anatomically correct position is only possible if the femur is pulled in the foot direction and thereby the soft tissue parts are stretched or if shortening of the femur is undertaken. Acute stretching by more than about 2 cm normally leads to damage to the sciatic nerve and thereby to functional failures. In the case of shortening of the femur, a significant leg length difference generally remains, along with dysfunction, because major muscle insertions have to be sacrificed.

Continuous lengthening procedures, which reduce the risk of nerve damage, were possible in the past only with external fixators, which were attached to the pelvis, for one thing, and to the femur, for another. However, these fixators are extremely stressful for the patient, and there is a significant risk of infection or at least of contamination, something that is particularly problematical in view of the subsequent hip endoprosthesis.

It is known to carry out leg lengthening procedures with fully implantable, motorized distraction marrow nails, as they are described, for example, in EP 1 371 346 A1. Now a further area of use of these distraction marrow nails is not only to lengthen a bone, but also to stretch the soft tissue parts, for example in order to displace the femur in the foot direction, as in the situation described above, in order to subsequently be able to implant a hip joint endoprosthesis in a regular position.

The first clinical uses in this regard, as described in "J Bone Joint Surg Vol. 87-B, No. 4, April 2005," already occurred more than ten years ago. The support apparatus used in this application comprises a mounting device that has a slot, into which the support end of the telescoping part of the distraction marrow nail was introduced, with the movement of the support end being greatly restricted and taking place in uncontrolled manner with regard to the lever effects.

The problem therefore lies in supporting the support end of the distraction marrow nail on the proximal side facing the pelvis, because here, on the one hand, sufficient axial forces have to be absorbed, but on the other hand, the scope of movement should be restricted as little as possible, because otherwise, the attachment of the apparatus would break out due to the lever forces of the leg.

SUMMARY OF THE INVENTION

The task underlying the invention now lies in implementing a support apparatus that is adapted to the anatomical conditions on the outside of the pelvic bone, and is attached in the lower region, where enough bone mass is present at the acetabular bone, in such a manner that the tensile forces and shear forces that occur here are absorbed, while the resulting pressure forces in the upper region are transferred over the full area. Furthermore, it holds true, on the one hand, that the greatest possible freedom of movement of the leg should be made possible, so that the lever forces resulting from the length of the leg (approximately 1 m) do not pull the fixation screws of the apparatus out of the pelvic bone and thereby lead to loosening, and on the other hand, no luxation (the joint partners moving away from one another) takes place.

The task underlying the invention is accomplished by means of a support apparatus having the characteristics of claim 1. Advantageous embodiments of the support apparatus according to the invention are the object of claims 2 to 11.

An apparatus provided with the support apparatus, for stretching of soft tissue parts in the hip region, comprises the characteristics of claim 12. A further apparatus for stretching soft tissue parts in the hip region comprises the characteristics of claim 13.

In the support apparatus according to the invention, which can be mounted on the pelvic bone, the mounting device comprises a ball seat having a cavity that forms a ball seat surface, for accommodating a ball provided at the support end of the telescoping part or of the anchoring part. The inside radius of the ball seat surface corresponds to the outside radius of the ball. The ball seat is configured and disposed in such a manner that the telescoping part or the anchoring part is able to perform a sufficient movement for an extensively normal movement pattern of the femur, and cannot luxate out of the ball seat when the telescoping part or the anchoring part is implanted in the femur.

Sufficient movement is guaranteed, for example, if the longitudinal axis of the telescoping part or of the anchoring part can move within a region of an imaginary cone having a cone angle of approximately 25-45°, preferably approximately 35°, when the anchoring part or the telescoping part is implanted in the femur and the support apparatus is mounted in the pelvic bone.

Preferably, at least two passage openings disposed at a distance from one another, distally with regard to the mounting device, are provided in the base plate. At these passage openings, the support apparatus is attached to the pelvic bone by means of spongiosa screws. This attachment is sufficient for being able to absorb tensile forces and for transferring pressure forces to the pelvic bone. Attachment openings proximal to the mounting device are therefore not necessary, but they can be provided for further stabilization. The proximal edge of the base plate can be pushed under the muscles that lie against the pelvic bone, without additional attachment being required here, because pressure forces primarily occur in this region.

In a preferred embodiment, the ball seat comprises a base, preferably formed by a support block, having a sub-cavity with a first partial ball seat surface, which is configured and disposed in such a manner that the ball can be freely laid into the sub-cavity. A covering with a second, small partial ball seat surface can be attached in such a manner that the first partial ball seat surface makes a transition into the second partial ball seat surface to form a total ball seat surface, with the total ball seat surface being larger than the external hemispherical surface of the ball. The covering thereby forms an undercut that prevents luxation of the ball out of the cavity of the ball seat.

In this case, sufficient security is guaranteed if the total ball seat surface is larger by 2% to 5% than the external hemispherical surface.

The inside circumference of the total ball seat surface must at least be larger at this location than half the circumference of the ball.

If the base plate is flattened at its proximal edge, the proximal edge of the base plate can be pushed under the muscles on the pelvic bone without risk of injury.

To reduce sliding friction, a plastic shell is preferably inserted into the cavity or a friction-reducing coating is applied to the ball or the cavity is coated with friction-reducing material.

BRIEF DESCRIPTION OF THE DRAWINGS

Exemplary embodiments of the invention will be explained in greater detail below, using drawings. These show:

FIG. 3, a median cross-section of the support apparatus of FIG. 1;

FIG. 4, an apparatus having the support apparatus, for stretching soft tissue parts in the implanted state, at the beginning of a treatment;

FIG. 5, the apparatus of FIG. 4 after stretching of the soft tissue parts toward the end of a treatment;

FIG. 6, a further apparatus having the support apparatus, for stretching soft tissue parts in the implanted state at the beginning of a treatment;

FIG. 7, the apparatus of FIG. 6 after stretching of the soft tissue parts toward the end of a treatment.

DETAILED DESCRIPTION

Figure 1:
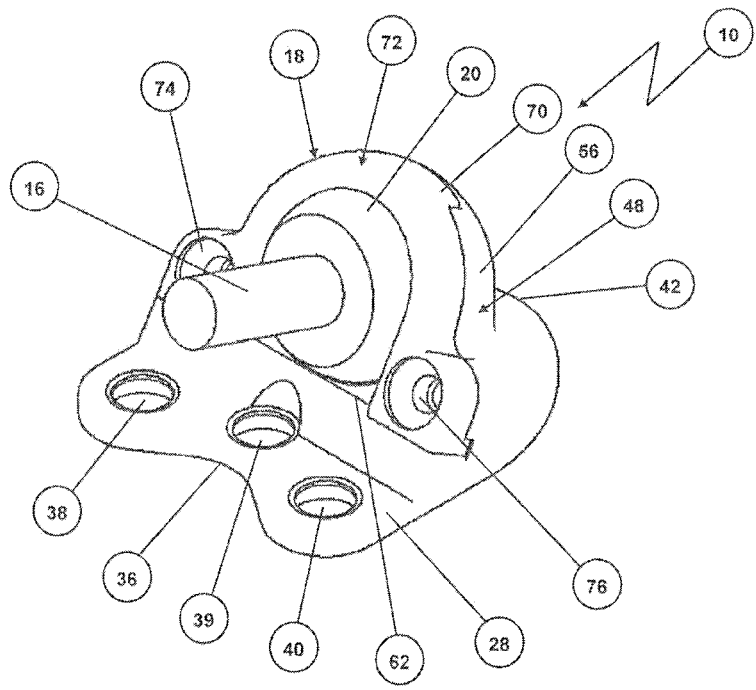
FIG. 1, a perspective view of a support apparatus according to the invention.

First, FIGS. 4 and 5 will be described. In FIGS. 4 and 5, the skeletal structure of a patient in the hip region is shown schematically, with the left thigh of the patient being displaced toward the head (in the cranial direction) in FIG. 4. This displacement can result from an incorrectly placed socket or after an accident event or after a tumor resection.

The pelvis 2 is disposed in the lower region of the torso 1. In FIG. 4, the joint head 9 is correctly disposed in the hip socket 7 at the upper end of the femur 6 of the right thigh 5. In the case of the left thigh 3 of the patient, the femur 4 has been displaced upward toward the head with reference to the hip socket 8.

In order to allow displacement of the femur 4 toward the foot and to stretch the corresponding soft tissue parts, a distraction marrow nail 12 is implanted in the femur 4, which nail comprises an anchoring part 14 that is implanted in the femur 4, in the longitudinal direction of the latter, which part is attached to the femur 4 by means of at least one attachment screw 22 disposed transversely. A telescoping part 16 is guided in the anchoring part 14 so as to be displaceable in the longitudinal direction of the anchoring part 14. A ball 20 is attached at the proximal end, i.e. the end facing the torso 1, of the telescoping part 16, for example by means of a conical press fit, which ball is mounted in a mounting device 18 of a support apparatus 10 in articulated manner. The support apparatus 10 is mounted on the iliac bone of the pelvis 2. The telescoping part 16 can be displaced in the proximal direction by means of a motor disposed in the anchoring part 14. To control the motor, the motor is connected with an antenna 24 disposed underneath the skin of the thigh, by way of a cable 26. A corresponding design of a marrow nail is known, for example, from EP 1 371 346 A1.

The telescoping part 16 is displaced in the proximal direction, step by step, over an extended period of time, by means of the motor. The telescoping part 16 is supported on the support device 10, during this process, by way of the ball 20 disposed at the proximal support end of the telescoping part 16, which ball is mounted in the mounting device 18 in articulated manner; the support device in turn is mounted on the iliac bone of the pelvis 2. In this way, the femur 4 is displaced in the distal direction, i.e. away from the torso 1, and at the same time, the soft tissue parts are stretched. Such a method for stretching the soft tissue parts is described in the document "J Bone Joint Surg Vol. 87-B, No. 4, April 2005," so that the method will not be described in any further detail below.

A further apparatus for stretching soft tissue parts will be described in connection with FIGS. 6 and 7. It shall be noted that the skeletal structure having a left thigh that has been displaced upward, as is illustrated in FIGS. 6 and 7, corresponds to the skeletal structure illustrated in FIGS. 4 and 5 and is denoted by the same reference numerals. To avoid repetitions, reference shall be made to the description of FIGS. 4 and 5 provided above.

The apparatus for stretching soft tissue parts includes a distraction marrow nail 12a implantable in the femur 4 and a support apparatus 10 for proximally supporting the distraction marrow nail 12a. The support apparatus 10 is identical to the support apparatus shown in FIGS. 4 and 5 and will be described in more detail hereafter in connection with FIGS. 1 and 3.

The distraction marrow nail 12a, in turn, comprises an anchoring part 14, a telescoping part 16 mounted displaceably in the anchoring part 14, and a drive disposed in the anchoring part 14 for linearly displacing the telescoping part 16 relative to the anchoring part 14. The drive comprises a motor and a gear unit. These are not shown in FIGS. 6 and 7. By actuating the drive, the telescoping part 16 can be extended and retracted in the longitudinal direction of the anchoring part 14. The control of the motor, in turn, takes place by way of a cable 26 and an antenna 24 disposed underneath the skin of the thigh.

The distraction marrow nail 12a thus comprises the same components as the distraction marrow nail 12 in FIGS. 4 and 5 and differs from the same in that the ball 20 for mounting on the support apparatus 10 is disposed at the end of the anchoring part 14 located opposite the telescoping part 16. Correspondingly, the apparatus for stretching soft tissue parts shown in FIGS. 6 and 7 differs from the apparatus shown in FIGS. 4 and 5 in that the distraction marrow nail 12a is movably mounted on the support apparatus 10 by way of the anchoring part 14 thereof, and the telescoping part 16 can be attached to the femur 4 by way of a transversely disposed fastening screw 22. Compared to the arrangement in FIGS. 4 and 5, the distraction marrow nail 12a in FIGS. 6 and 7 is thus disposed rotated by 180°. FIG. 6 shows the apparatus for stretching soft tissue parts in the implanted state at the beginning of a treatment. The telescoping part is in a retracted position. Only the distal end of the telescoping part 16 protrudes from the distal end of the anchoring part 14 and is attached to the femur by way of a nail 22. So as to allow a displacement of the femur 4 toward the foot and stretch the corresponding soft tissue parts, the telescoping part 16 can be incrementally displaced in the distal direction (that is away from the torso 1) by way of the motor. As a result of the incremental extension of the telescoping part 16, the femur 4 is displaced in the distal direction. The apparatus shown in FIGS. 6 and 7 thus achieves the same result as the apparatus in FIGS. 4 and 5. The only difference is the orientation and mounting of the distraction marrow nail 12a, which in the embodiment shown in FIGS. 6 and 7 is attached with the telescoping part 16 thereof to the femur 4 and movably mounted in the mounting device 10 with a ball 12 affixed to the proximal end of the anchoring part 14.

Figure 8:
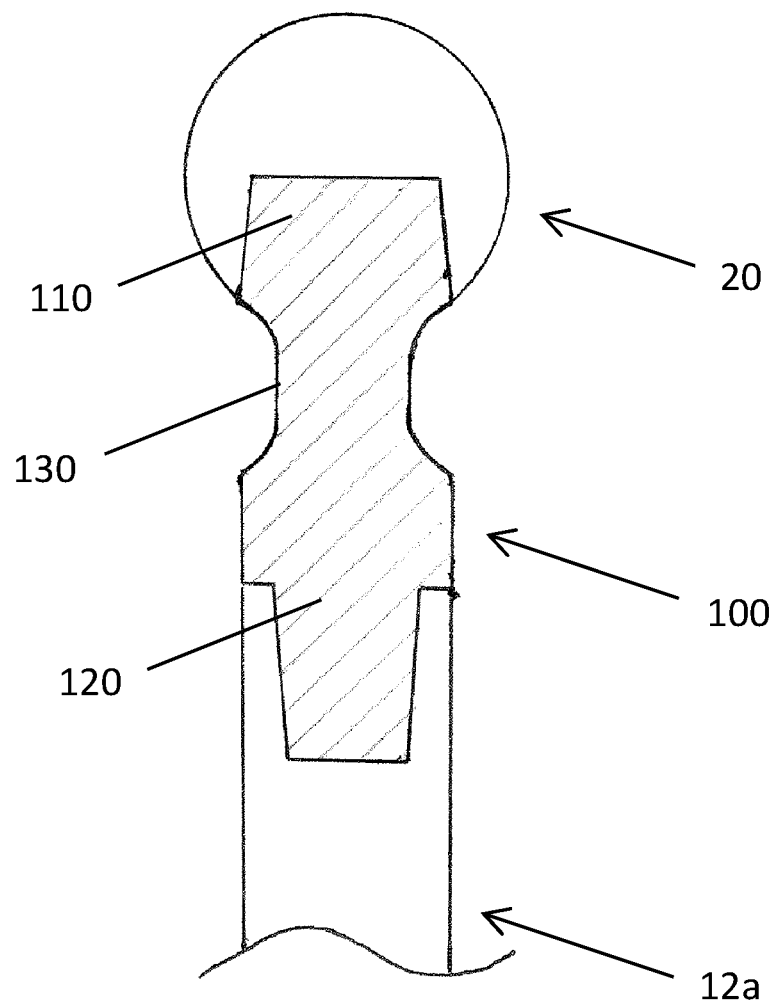
FIG. 8, a partial section of a distraction marrow nail between an intermediate piece for movable mounting in the support apparatus of FIG. 1.

According to one implementation, the distraction marrow nail 12a described in connection with FIGS. 6 and 7 can furthermore comprise an intermediate piece 100 disposed between the ball 20 and the proximal end of the distraction marrow nail 12a. The position of the intermediate piece 100 is indicated in FIG. 6. FIG. 8 schematically shows the proximal end of the distraction marrow nail 12a together with the intermediate piece 100 and the ball 20.

The intermediate piece 100 is attached with its distal end 120 to the anchoring part 14 of the distraction marrow nail 120a. For this purpose, the intermediate piece 100 can be connected to the proximal end of the anchoring part 14 in a form-locked or integral manner. At the proximal end 110 of the intermediate piece 100, furthermore the ball 20 is attached for movable mounting in the support apparatus 10. The intermediate piece 100, together with the ball 20, thus forms the support end of the distraction marrow nail 12a. By using the intermediate piece 100, a conventional distraction marrow nail can thus be used to implement the apparatus for stretching soft tissue parts described in connection with FIGS. 6 and 7. The conventional distraction marrow nail only has to be provided with the intermediate piece 100 with the ball 20 described herein.

According to the embodiment shown in FIG. 8, the ball 20 is attached to the rod-shaped proximal end of the intermediate piece 100 and rigidly connected thereto. Alternatively, it is also conceivable that the ball 20 is designed as a one-piece support element together with the intermediate piece 100. Independently of the one-piece or two-piece design described herein, according to one advantageous embodiment the intermediate piece 100 can furthermore have a constriction 130 extending in the circumferential direction of the intermediate piece 100 (see FIG. 8), which is disposed (directly) behind the ball 20 on the intermediate piece 100, considered from the proximal end. As a result of this constriction 130 at the intermediate piece 130, the scope of movement of the distraction marrow nail relative to the support apparatus 10 is further increased.

Figure 2:
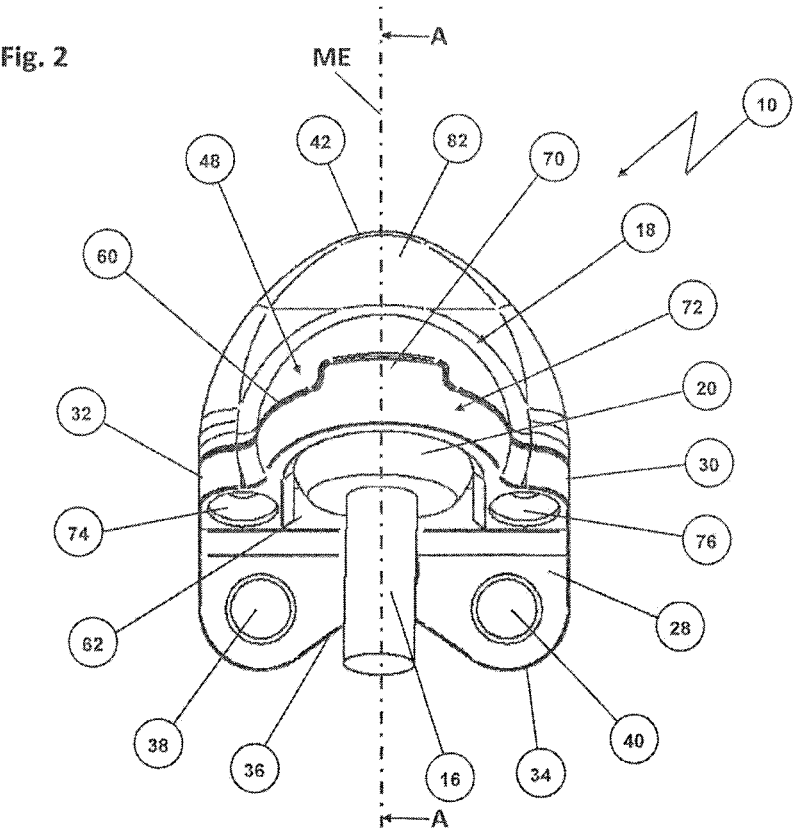
FIG. 2, a top view of the support apparatus of FIG. 1.

The structure of the support apparatus 10 and mounting of the ball 20 of the telescoping part 16 or of the anchoring part 14 in the mounting device 18 is shown in detail in FIGS. 1 to 3.

The support apparatus 10 is configured symmetrically with reference to a center plane ME that runs perpendicular to the plate plane. In the following, the terms "proximal" and "distal" will be used with regard to the placement of individual elements, with proximal meaning facing the torso 1 and distal meaning facing away from the torso 1.

The support apparatus 10 comprises a base plate 28 that has two side edges 30, 32, which run parallel to one another and parallel to the center plane ME in the distal section, and subsequently run curved toward the center plane ME in the proximal direction, so that they form a rounded-off front tip 42 at the intersection point with the center plane ME. In the distal side edge 34, which runs perpendicular to the center plane ME, in total, an indentation 36 is formed in the center. On both sides of the center line ME, two passage openings 38, 40 pass through the base plate 28 adjacent to the distal side edge 34. A further passage opening 39 is configured in the center between the passage openings 38 and 40.

Proximal to the passage openings 38, 39, 40, a mounting device 18 is provided on the base plate 28, which device comprises a ball seat 48, in which a cavity 58 is configured, in which the ball 20 is mounted on the support end of the telescoping part 16 or at the support end of the anchoring part 14.

The ball seat 48 consists of two elements, which each form a partial ball seat surface. A support block 56 extends upward from the top of the base plate 28. A sub-cavity 84 is configured in the support block 56, which cavity defines a first partial ball seat surface. The sub-cavity 84 is open in the distal direction, and is delimited by a face edge 60 that runs perpendicular to the center plane ME.

As can be seen in FIG. 3, the ball sector of the spherical section of the sub-cavity 84 is slightly smaller than the hemisphere sector of the ball 20 of the telescoping part 16 or of the ball of the anchoring part 14. The surface of a slanted step 62 extends from the lower end of the spherical part of the sub-cavity 84, essentially tangentially in the distal direction, at an upward slant.

The sub-cavity 84 of the support block 56 is therefore configured in such a manner that the ball 20 of the telescoping part 16 or of the anchoring part 14 can be laid into the sub-cavity 84 if no covering 72 is affixed, without the ball 20 having to be acutely displaced in the distal direction.

The covering 72 is affixed to the face side of the support block 56. The covering 72 is essentially configured in U shape and lies on the slanted step 62 with the free ends of its shanks. A passage opening 74 and 76 is configured at the ends of the two free shanks, in each instance, through which openings the attachment screws can pass, which screws attach the covering 72 to the support block 56. The inside of the covering 72 forms a second partial ball seat surface 86 in the upper, arc-shaped region, which surface follows flush with the partial ball seat surface of the cavity 58, thereby increasing the total ball seat surface in such a manner that it is larger than the hemispherical surface of the ball 20. In other words, an undercut is formed by the covering 72, which undercut prevents the ball 20 from being able to luxate out of the ball seat 48 when the covering 72 is affixed to the support block 56.

For firm anchoring of the covering 72 on the support block 56, a groove 64 is configured in the top section of the support block 56, adjacent to the face edge 60, thereby defining an edge projection 66 at the edge 60. At the same time, an engagement shank 70 having an engagement groove 68 is configured in the covering 72, which groove engages into the groove 64 by way of the edge projection 66. By means of the formation of the engagement groove 68, an engagement shank 70 is thereby formed at the proximal edge of the covering 72, which shank engages into the groove 64.

In this way, a shape-fit connection of the covering 72 with the support block 56 is created when the covering 72 is attached to the support block 56 by means attachment screws that pass through the passage openings 74, 76.

In order to reduce the slide friction between the ball 20 in the cavity 58 of the ball seat 48, a plastic shell 50 is disposed in the cavity 58, which shell lies against the seat surface. A projection 52 is configured on the plastic shell 50, in the proximal region, which projection engages into a recess 54 in the cavity 58, thereby preventing spherical displacement of the plastic shell and guaranteeing secure hold of the plastic shell 50 in the cavity 58. The plastic shell 50 thereby forms the actual cavity, the inside diameter of which corresponds to the outside diameter of the ball 20.

The ball seat 48 in total is configured in such a manner that the longitudinal axis LT of the telescoping part 16 or of the anchoring part 14 can move within a range of an imaginary cone having a cone angle of 25-45°, preferably 35°, when the anchoring part 14 or the telescoping part 16 is implanted in the femur 4 and the support apparatus 10 is mounted on the pelvic bone 2.

Proximal to the mounting apparatus 18, the base plate 28 is flattened toward the tip 42, thereby making it possible to push the tip 42 under the muscles that lie against the pelvic bone without any risk of injury.

In particular, the base plate 28 is designed as a flat plate, which has a flat plate side (that is flat plate back side) located opposite the mounting device 18. The support apparatus 10 can thus be placed with the flat back side of the base plate against the pelvic bone and attached thereto. At the same time, the mounting device 18 disposed on the base plate front side allows the ball 20 to be movably mounted so as to ensure good movability of the distraction marrow nail 12, 12a in the frontal and sagital planes.

The base plate 28, together with the mounting device 18 except for the covering 72, preferably forms one part, with all the borders and edges being rounded off in order to minimize the risk of injury.

The base plate 28, with the mounting device 18 and the covering 72, is preferably formed from steel or titanium. The plastic shell 50 is preferably formed from PTFE or PEEK.

REFERENCE SYMBOL LIST

1 - torso
2 - pelvic bone
3 - left thigh
4 - left femur
5 - right thigh
6 - right femur
7 - right hip socket
8 - left hip socket
9 - joint head
10 - support apparatus
12, 12a - distraction marrow nail
14 - anchoring part
16 - telescoping part
18 - mounting device
20 - ball
22 - screw
24 - antenna
26 - cable
28 - base plate
30 - right side edge
32 - left side edge
34 - distal side edge
36 - indentation
38 - passage opening
39 - passage opening
40 - passage opening
42 - tip
48 - ball seat
50 - plastic shell
52 - projection
54 - recess
56 - support block
58 - cavity
60 - face edge
62 - slanted step
64 - groove
66 - edge projection
68 - engagement groove
70 - engagement shank
72 - covering
74 - passage opening
76 - passage opening
82 - flattened part
84 - sub-cavity
86 - partial ball seat surface
100 - intermediate piece
110 - intermediate piece, proximal end
120 - intermediate piece, distal end
130 - constriction

I claim:

1. An apparatus for stretching soft tissue parts in the hip region, comprising:
   a distraction marrow nail that has a proximal anchoring part, and a distal telescoping part that can be moved in the longitudinal direction with reference to the anchoring part, wherein the anchoring part at its proximal end located opposite the telescoping part comprises a support end having a ball; and
   a support apparatus mountable on the pelvic bone for supporting the support end of the distraction marrow nail, wherein the support apparatus comprises a base plate attachable to the pelvic bone and a mounting device provided on the base plate for movably mounting the support end of the distraction marrow nail,
   wherein the mounting device comprises a ball seat having a cavity that forms a ball seat surface for mounting the ball, wherein the inside radius of the ball seat surface corresponds to the outside radius of the ball, and wherein the ball seat is configured and disposed in such a manner that the distraction marrow nail can perform a movement sufficient for an extensively normal movement pattern of the femur and cannot luxate out of the ball seat when implanted in the femur.

2. The apparatus of claim 1, wherein the ball seat is configured in such a manner that the longitudinal axis of the distraction marrow nail can move within a range of an imaginary cone having a cone angle of 25-45°, preferably approximately 35°, when the distraction marrow nail is implanted in the femur and the support apparatus is mounted on the pelvic bone.

3. The apparatus of claim 1, wherein at least two passage openings disposed at a distance from one another are provided in the base plate, distally with reference to the mounting device.

4. The apparatus of claim 1, wherein the ball seat comprises a base having a sub-cavity with a first partial ball seat surface, which is configured and disposed in such a manner that the ball can be freely laid into the sub-cavity, and comprises a covering having a second partial ball seat surface, which can be attached in such a manner that the first partial ball seat surface makes a transition into the second partial ball seat surface to form a total ball seat surface, wherein the total ball seat surface is larger than the external hemispherical surface of the ball.

5. The apparatus of claim 4, wherein the total ball seat surface is 5% to 10% larger than the external hemispherical surface.

6. The apparatus of claim 1, wherein the base plate is flattened at its proximal edge.

7. The apparatus of claim 1, wherein in order to reduce the slide friction, a plastic shell is inserted into the cavity or a friction-reducing coating is applied to the ball or the cavity is coated with friction-reducing material.

8. The apparatus of claim 1, wherein the base plate has a first side facing the pelvic bone and a second side facing away from the pelvic bone, wherein the mounting device is arranged on the second side.

9. The apparatus of claim 1, wherein the distraction marrow nail at the support end thereof comprises an intermediate piece for accommodating the ball.

10. The apparatus of claim 9, wherein the intermediate piece comprises a constriction extending in the circumferential direction, which is disposed directly behind the ball on the intermediate piece, considered from the proximal end.

\* \* \* \* \*